United States Patent [19]

Khramov

[11] Patent Number: 5,777,157
[45] Date of Patent: Jul. 7, 1998

[54] PROCESS FOR PRODUCTION AND PURIFICATION OF TRIACETIN

[75] Inventor: Mikhail Khramov, San Luis Potosi, Mexico

[73] Assignee: Industrias Monfel S.A. de C.V., Mexico

[21] Appl. No.: 584,955

[22] Filed: Jan. 11, 1996

[51] Int. Cl.[6] .................................................. C07C 69/18
[52] U.S. Cl. ........................................ 560/248; 560/263
[58] Field of Search .................................... 560/248, 263

[56] References Cited

U.S. PATENT DOCUMENTS

| | | | |
|---|---|---|---|
| 1,536,545 | 5/1925 | Willkie | 560/248 |
| 1,869,954 | 8/1932 | Camarius et al. | 560/248 |
| 2,165,450 | 7/1939 | Burke et al. | 560/248 |
| 2,913,492 | 11/1959 | van der Voort | 260/571 |
| 3,108,133 | 10/1963 | Trevoy et al. | 560/248 |
| 4,381,407 | 4/1983 | Bremus et al. | 560/263 |
| 4,729,818 | 3/1988 | Berg | 562/608 |
| 5,371,279 | 12/1994 | Qi et al. | 560/263 |
| 5,387,713 | 2/1995 | Cook et al. | 562/608 |
| 5,399,751 | 3/1995 | Gentry et al. | 562/608 |

FOREIGN PATENT DOCUMENTS

| | | |
|---|---|---|
| 2900023 | 7/1980 | Germany. |
| 0152333 | 11/1981 | Germany. |
| 156804 | 9/1982 | Germany. |
| 535286 | 1/1977 | U.S.S.R. |

*Primary Examiner*—Bernard Dentz
*Attorney, Agent, or Firm*—Speckman Pauley Petersen & Fejer

[57] ABSTRACT

A method for producing and purifying triacetin. The method includes an initial separation of triacetin from a crude composition of triacetin and impurities. The separated triacetin is then contacted with an aqueous solution containing an oxidant, and results in an odorless and colorless purified triacetin.

18 Claims, 1 Drawing Sheet

PROCESS FOR PRODUCTION AND PURIFICATION OF TRIACETIN

BACKGROUND OF THE INVENTION

1. Field of the Invention

This invention relates to a process for producing and purifying triacetin. The process includes an initial separation of triacetin from a composition of triacetin and impurities, and then contacting the relatively pure triacetin with an aqueous solution containing a relatively strong oxidant.

2. Description of Prior Art

Triacetin has become a relatively important chemical in manufacturing and is used in many industries, including the food, drug, and plastics industries. Triacetin is commonly prepared by esterification of glycerol with acetic anhydride or acetic acid, or by reacting ketene with glycerol, or by the oxidation of allyl acetate in the presence of acetic acid. Crude triacetin typically contains acetic acid, acetic anhydride and smaller quantities of other impurities. Volatile impurities such as acetic anhydride and acetic acid are usually removed by distillation. The remaining triacetin is then usually distilled to remove nonvolatile impurities and to eliminate color and odor. However, distillation generally requires relatively high temperatures that initiate additional reaction products, and thus even after distillation, triacetin typically has an odor and a yellow color, both of which must be eliminated for the triacetin to qualify as pure triacetin.

Several processes exist for eliminating the color and odor associated with crude triacetin. U.S. Pat. No. 3,108,133 teaches a process for purifying triacetin which includes an initial flash distillation to remove the majority of excess acetic acid. The initial distillation is conducted first at atmospheric pressure, and in the later stages at subatmospheric pressures. A major portion of acetic acid is removed in the initial distillation step. A second distillation is then conducted at high temperature and low pressure and triacetin is recovered overhead. A third distillation is then conducted in the presence of water to take off additional acetic acid, and the bottoms of such distillation are recovered.

Other conventional processes for purifying triacetin include contacting the triacetin solution with activated carbon. U.S.S.R. Patent 535286 teaches a process for purifying crude triacetin by distilling off acetic acid, treating the resulting triacetin with an aqueous solution of sodium bicarbonate and sodium sulfate, and passing the resulting organic layer of triacetin through a column packed with activated carbon. German Patent 0152 333 teaches a process for purifying triacetin which includes adding sodium carbonate or sodium bicarbonate to partially purified triacetin, eliminating water with a vacuum distillation and contacting the resulting triacetin with activated carbon. In both of the above processes sodium bicarbonate or sodium carbonate is used to neutralize the triacetin, and activated carbon is used to substantially reduce the color. However, activated carbon is relatively costly.

German Reference 29 00 023 discloses a method for purifying triacetin which includes treating crude triacetin for 0.5 to 5 hours with water steam at 3–14 mbar and 100° C.–130° C. The resulting solution is then treated with an inert gas such as nitrogen and/or carbon dioxide.

German Reference 1568 04 teaches a process for purifying triacetin which includes reacting a solution of crude triacetin with a lower alcohol such as methanol or ethanol, heating the solution to approximately 145° C. and distilling off excessive alcohol and other reaction products until the temperature of the solution reaches the boiling point of triacetin. Such process must be conducted carefully because alcoholysis of triacetin occurs in which diacetin isomers and lower alcohol acetate are readily formed.

U.S. Pat. No. 4,381,407 patent teaches a continuous process for preparing triacetin which includes charging liquid glycerol into a top portion of a reaction column having a plurality of plates, and charging acetic acid and acetic anhydride vapors into a bottom portion of the column. The reaction occurs in a counter current mode, and is conducted at 100° C. to 250° C. and from 0.2 bar to 30 bar. The resulting product is then purified by distillation in a rectification column.

U.S. Pat. No. 5,387,713 teaches a process for purifying carboxylic acids having iodide and oxidizable impurities by contacting the solution with hydrogen peroxide and recovering the purified carboxylic acids by distillation or evaporation.

U.S. Pat. No. 2,913,492 teaches a process for removal of formic acid from mixtures of formic acid and other organic components. The process includes contacting the solution with a catalytic ingredient such as chromium oxide and copper oxide which decomposes the formic acid into $CO_2$ and $H_2$.

U.S. Pat. No. 5,399,751 teaches a method for recovering carboxylic acids such as formic acid and acetic acid from aqueous solutions. The method includes contacting the aqueous solution with a solvent consisting essentially of mixed trialkylphosphine oxides in a counter-current liquid-liquid extraction flow.

U.S. Pat. No. 5,371,279 teaches a method for removing acetic acid from liquid ether acetates by contacting the liquid ether acetates with alumina.

U.S. Pat. No. 4,729,818 teaches a process for separating acetic acid from water. The process includes adding an acid such as benzoic acid or hexanoic acid to the acetic acid and water mixture. The addition of such an acid to the mixture improves the relative volatility of the water to the acetic acid and allows separation of the water from acetic acid by distillation.

Thus, the teachings above, and others known to us require either multiple distillations at relatively high temperatures and relatively low pressures, or require the use of costly activated carbon to achieve pure triacetin. It is apparent that there is a need for a relatively inexpensive process which does not require activated carbon, nor excessive heat and high vacuum distillation to purify triacetin.

SUMMARY OF THE INVENTION

It is one object of this invention to provide a process for producing and purifying triacetin without a need for relatively costly activated carbon.

It is another object of this invention to provide a process for purifying triacetin which achieves colorless and odorless triacetin.

These and other objects are achieved in a process for purifying triacetin which includes initially separating the triacetin from the major portion of the impurities inherent in crude triacetin, such as acetic acid and acetic anhydride, and then contacting the resulting triacetin with an oxidant to eliminate any residual odor and color. According to one preferred embodiment of this invention, the crude triacetin is passed through a column packed with members, such as glass rings. The column is preferably heated between about 100° C. to about 130° C., and has a pressure between about 20 mm Hg to about 50 mm Hg. The majority of the impurities is withdrawn from the overhead of the column, while partially purified triacetin is continuously withdrawn from the bottom of the column.

The partially purified triacetin is then preferably contacted with an aqueous solution containing a relatively strong oxidant. Suitable oxidants include sodium, potassium, calcium or other metal hypochlorites, permanganates, peroxodisulfates, chromates, hydrogen peroxide, chlorine, ozone and other strong oxidants. Preferably the oxidant is about 0.5% to about 5.0% by weight of the aqueous solution.

According to another preferred embodiment of this invention, the aqueous solution also includes an alkali or alkali earth metal hydroxide, or a salt of an alkali or an alkali earth metal and a weak acid. Such embodiment not only removes color and odor, but also reduces any residual acidity.

If necessary, the resulting relatively pure triacetin can then be passed through a column again to eliminate any residual water content.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Figure 1:
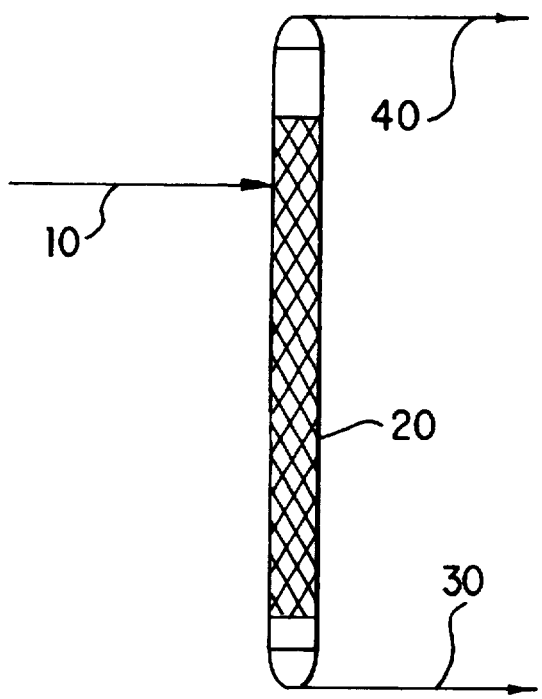
FIG. 1 is a schematic representation of a column which can be used in the process according to one preferred embodiment of this invention.

The process for producing and purifying triacetin according this invention achieves relatively odorless and colorless triacetin which has a relatively low acidity. The process according to this invention uses an aqueous solution comprising a relatively strong oxidant, rather than relatively expensive activated carbon to achieve such pure triacetin. The process according to this invention can also include one or more distillations at relatively low temperatures, such as about 100° C. to about 130° C. Such relatively low temperatures avoid the production of additional reaction products during the distillation.

The method of producing crude triacetin according to this invention can include charging acetic anhydride to a reactor, adding glycerol at such a rate that the temperature inside the reactor does not exceed about 120° C. to about 130° C., and distilling off a portion of the acetic acid formed in the reaction. It should be noted that this is not the only manner of producing crude triacetin suitable for the process of purifying triacetin according to this invention. Crude triacetin produced by many other known methods can be used in the process for purifying triacetin according to this invention.

According to one preferred embodiment of this invention, triacetin is separated from the crude triacetin composition comprising triacetin, acetic anhydride, and other impurities to obtain partially purified triacetin. FIG. 1 shows a diagram of a rectification column which can be used to accomplish such separation. Crude triacetin enters the top portion of column 20 through line 10. Acetic acid, acetic anhydride and other volatile impurities are drawn from the overhead through line 40. Partially purified triacetin is withdrawn through line 30. This process can be either batch or continuous.

According to one preferred embodiment of this invention, column 20 can be heated, preferably to a temperature between about 100° C. to about 130° C. Column 20 can be packed with members such as glass rings or glass beads. Column 20 preferably has an internal pressure between about 20 mm Hg to about 50 mm Hg.

According to the method of this invention, partially purified triacetin recovered from line 30 is then contacted with a relatively strong oxidant. The oxidant is preferably in an aqueous solution. Any conventional vessel can be used to bring the partially purified triacetin in contact with the oxidant-containing aqueous solution. Such vessel preferably includes an agitator to facilitate contact among the liquids.

The resulting solution can undergo a second distillation, if necessary, to eliminate any residual water.

The oxidant used is preferably soluble in water and does not decompose triacetin. Suitable oxidants include sodium, potassium, calcium or other metal hypochlorites, permanganates, peroxodisulfates, chromates or dichromates, hydrogen peroxide, chlorine, ozone, and mixtures of one or more of such oxidants. The primary consideration regarding the oxidant is its solubility in water and the stability of triacetin under the particular process conditions. According to one preferred embodiment of this invention, the aqueous solution comprises about 0.5% to about 5.0% by weight of oxidant.

The ratio of partially purified triacetin to aqueous solution should be sufficient to ensure separation of the aqueous and organic phases. According to one preferred embodiment of this invention, the weight ratio of partially purified triacetin to aqueous solution is from about 1:4 to about 4:1. The pH of the aqueous solution can be modified with the addition of an acid such as 1% $H_2SO_4$ or 1% HCl, for example, so as to ensure the oxidation of the impurities contained in the triacetin.

According to one preferred embodiment of this invention, an alkali metal hydroxide or alkali earth metal hydroxide is added to the aqueous solution. According to another preferred embodiment of this invention, a salt of an alkali metal and a weak acid, or a salt of an alkali earth metal and a weak acid are added to the aqueous solution. Suitable alkali metal hydroxides or alkali earth metal hydroxides include sodium hydroxide, potassium hydroxide, lithium hydroxide, calcium hydroxide and magnesium hydroxide. Suitable salts of an alkali metal or an alkali earth metal and a weak acid include carbonates, bicarbonates, and silicates of sodium, potassium, lithium, calcium and magnesium. Addition of such alkali elements to the aqueous solution also reduces any residual acidity of the triacetin.

The time for which the partially purified triacetin should be contacted with the oxidant-containing aqueous solution can vary depending upon the purity of the original crude triacetin, the concentration and nature of the oxidant, the pH of the aqueous solution and the construction of the vessel in which the reaction takes place. Generally from about 5 to about 15 minutes is sufficient to purify triacetin. The temperature of the solution is preferably from about 0° C. to about 30° C. Although higher temperatures can be used, it should be noted that such higher temperatures can lead to degradation of triacetin.

All parts and percentages specified in the Examples below are by weight.

EXAMPLE 1

1.51 parts of glycerol were added to a reboiler containing 5.82 parts of acetic anhydride at a rate such that the temperature of the solution never exceeded 130° C. Acetic acid formed in the reaction was removed overhead. Th mixture was maintained at 125° C. to 130° C. for approximately three hours. The composition of the mixture as determined by gas chromatography was:

TABLE 1

| triacetin | diacetin | acetic acid | acetic anhydride | water | color APHA |
|---|---|---|---|---|---|
| 83.1 | 0.19 | 11.6 | 5.0 | 0.009 | 100 |

The mixture had a yellow color and a strong odor of acetic acid and acetic anhydride. The mixture was then passed through an oil-jacketed column packed with glass rings which was heated to about 130° C. and had an absolute pressure of about 50 mm Hg. The composition of the mixture withdrawn from the bottom portion of the column was:

TABLE 2

| triacetin | diacetin | acetic acid | acetic anhydride | water | color APHA |
|---|---|---|---|---|---|
| 99.2 | 0.23 | 0.53 | 0 | 0.007 | 130 |

One part of the resulting mixture was treated in a separation funnel with 1 part of an aqueous solution containing 2% of NaOH and 1% of $H_2O_2$. The color of the purified triacetin was 5–10 APHA, and acidity as acetic acid was 0.012%.

EXAMPLE 2

A mixture of triacetin was prepared by reacting glycerol with ketene, and distilling the mixture at 20 mm Hg to 30 mm Hg and at about 150° C. The composition of the product was:

TABLE 3

| triacetin | diacetin | acetic acid | acetic anhydride | water | color APHA |
|---|---|---|---|---|---|
| 99.2 | 0.35 | 0.4 | 0 | 0.008 | 25–30 |

One part of this solution was treated with one part of an aqueous solution containing one percent of sodium hypochlorite. A second solution of triacetin with a color of APHA 320 and otherwise having a very similar composition as the first solution described above, was treated with an identical aqueous solution. Results of the analysis are shown in Table 4.

A comparative analysis was conducted on each of the two solutions of triacetin in which each of solution of triacetin was treated with one part water rather than an oxidant-containing aqueous solution. The triacetin from the batch having an APHA color of 25–30 had an APHA color of 20 after such water treatment. The water treatment did not affect the APHA color of the triacetin from the batch having an APHA color of 320.

EXAMPLES 3–9

Table 4 shows the results of Examples 3–9. The triacetin used in Examples 3–9 was from the same two batches of triacetin used in Example 2. Table 4 shows the results obtained after using different compositions of aqueous solutions according to this invention, on each of the two batches of triacetin. Which batch of triacetin was used in a particular example can be determined by the APHA number in the "color before treatment" column of Table 4.

TABLE 4

| number of example | composition of aqueous solution | color before treatment | color after treatment |
|---|---|---|---|
| 2 | 1% NaClO | 25–30 | 10 |
| 2 | 1% NaClO | 320 | 50 |
| 3 | 1% NaClO 1% $Na_2CO_3$ | 25–30 | 5 |
| 3 | 1% NaClO 1% $Na_2CO_3$ | 320 | 40 |
| 4 | 1% NaClO 1% $NaHCO_3$ | 25–30 | <5 |
| 4 | 1% NaClO 1% $NaHCO_3$ | 320 | 50 |
| 5 | 1% NaClO 1% HCl | 25–30 | 10 |
| 5 | 1% NaClO 1% HCl | 320 | 100 |
| 6 | 1% $H_2O_2$ | 25–30 | 15 |
| 6 | 1% $H_2O_2$ | 320 | 80 |
| 7 | 1% $H_2O_2$ 1% KOH | 25–30 | 0 |
| 7 | 1% $H_2O_2$ 1% KOH | 320 | 80 |
| 8 | 1% $KMnO_4$ 1% $NaHCO_3$ | 25–30 | 10 |
| 9 | 1% $KMnO_4$ 1% $H_2SO_4$ | 25–30 | 15 |

EXAMPLE 10

Triacetin was prepared as set forth in Example 1. Crude triacetin with color APHA 130 was treated with an aqueous solution containing 4% $Na_2CO_3$ and 1% $H_2O_2$. The product was then passed through an oil-jacketed column packed with glass rings at 120° C. to 130° C. and at approximately 30 mm Hg absolute pressure. The composition of the purified triacetin was:

TABLE 5

| triacetin | diacetin | acidity as acetic acid | humidity | color APHA | odor |
|---|---|---|---|---|---|
| 99.6 | 0.33 | 0.02 | 0.02 | 10 | none |

EXAMPLE 11

Triacetin was prepared as set forth in Example 1. Crude triacetin with color APHA 130 was treated with an aqueous solution containing 4% $NaHCO_3$ and 1% NaClO. The product was then passed rough an oil-jacketed column packed with glass rings at 120° C. to 130° C. and at approximately 30 mm Hg absolute pressure. The composition of the purified triacetin was:

TABLE 6

| triacetin | diacetin | acidity as acetic acid | humidity | color APHA | odor |
|---|---|---|---|---|---|
| 99.77 | 0.04 | 0.009 | 0.007 | 10 | none |

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A process for purifying a composition of triacetin and impurities comprising the steps of:
   separating the triacetin from the composition forming a partially purified triacetin solution comprising at least one of acetic acid and acetic anhydride; and contacting the partially purified triacetin solution with an oxidant solution forming purified triacetin.

2. A process according to claim 1 further comprising separating the triacetin by passing the composition through a column.

3. A process according to claim 2 wherein the column is heated between about 100° C. to about 130° C.

4. A process according to claim 2 wherein the column contains a plurality of members.

5. A process according to claim 4 wherein the members comprise one of glass rings and glass beads.

6. A process according to claim 4 wherein the column is oil-jacketed.

7. A process according to claim 2 wherein an internal pressure of the column is between about 20 mm Hg to about 50 mm Hg.

8. A process according to claim 1 wherein the oxidant solution comprises an aqueous solution.

9. A process according to claim 1 wherein the oxidant solution comprises at least one of an alkali metal hydroxide and an alkali earth metal hydroxide.

10. A process according to claim 1 wherein the oxidant solution comprises a salt of one of an alkali metal or an alkali earth metal and a weak acid selected from the group consisting of sodium carbonate, sodium bicarbonate, sodium silicate, potassium carbonate, potassium bicarbonate, potassium silicate, lithium carbonate, lithium bicarbonate, lithium silicate, and calcium bicarbonate.

11. A process according to claim 9 wherein the at least one of an alkali metal hydroxide and an alkali earth metal hydroxide is selected from the group consisting of sodium hydroxide, potassium hydroxide, lithium hydroxide, calcium hydroxide, magnesium hydroxide and mixtures thereof.

12. A process according to claim 1 wherein an oxidant of the oxidant solution is selected from the group consisting of a permanganate, a hypochlorite, a peroxodisulfate, a chromate, a dichromate and a peroxide of at least one of an alkali metal and an alkali earth metal, and mixtures thereof.

13. A process according to claim 1 wherein an oxidant of the oxidant solution is selected from the group consisting of hydrogen peroxide, chlorine, ozone and mixtures thereof.

14. A process according to claim 1 wherein the oxidant solution comprises an aqueous solution, the triacetin is contacted with the aqueous solution, and the resulting solution is maintained between about 0° C. to about 30° C.

15. A process according to claim 1 further comprising distilling the purified triacetin in a heated rectification column.

16. A process for purifying triacetin comprising the steps of:

passing a mixture of unpurified triacetin through an oil-jacketed column packed with a plurality of members forming a partially purified triacetin solution comprising at least one of acetic acid and acetic anhydride; and contacting the partially purified triacetin solution with an aqueous solution comprising an oxidant selected from the group consisting of a permanganate, a hypochlorite, a peroxodisulfate, a chromate, a dichromate and a peroxide of at least one of an alkali metal and an alkali earth metal, and mixtures thereof.

17. A process for producing triacetin comprising the steps of:

reacting glycerol with one of acetic acid, acetic anhydride, and ketene forming a solution of crude triacetin;

passing the crude triacetin through a column packed with a plurality of members and heated between about 100° C. to 130° C. forming a partially purified triacetin solution comprising at least one of acetic acid and acetic anhydride; and contacting the partially purified triacetin solution with an aqueous oxidant solution.

18. A process according to claim 17 wherein the oxidant is selected from the group consisting of a permanganate, a hypochlorite, a peroxodisulfate, a chromate, a dichromate and a peroxide of at least one of an alkali metal and an alkali earth metal, and mixtures thereof.

* * * * *